(12) United States Patent
Chandler et al.

(10) Patent No.: US 6,764,383 B1
(45) Date of Patent: Jul. 20, 2004

(54) METHODS AND APPARATUSES FOR PROCESSING MICROFEATURE WORKPIECE SAMPLES

(75) Inventors: Phillip L. Chandler, Meridian, ID (US); Mark J. Fiechter, Boise, ID (US); Colin A. Green, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 10/448,916

(22) Filed: May 30, 2003

(51) Int. Cl.[7] .............................................. B24B 1/00
(52) U.S. Cl. .................. 451/28; 451/364; 451/365; 451/367; 451/369; 451/380; 451/177
(58) Field of Search .................. 451/28, 364, 365, 451/367, 369, 380, 177

(56) References Cited

U.S. PATENT DOCUMENTS 3,835,590 A * 9/1974 Hoffman ..................... 451/256
5,882,156 A * 3/1999 Hetzler ....................... 409/132

* cited by examiner

Primary Examiner—Joseph J. Hail, III
Assistant Examiner—Shantese McDonald
(74) Attorney, Agent, or Firm—Perkins Coie LLP

(57) ABSTRACT

Methods and apparatuses for processing microfeature workpiece samples are disclosed herein. An apparatus in accordance with one embodiment of the invention includes a support body, a first contact surface portion, a second contact surface portion, and a sample holder configured to releasably carry the microfeature workpiece sample. The sample holder can be movable relative to the support body between a first position and a second position, wherein the sample holder has a first orientation relative to the first and second contact surface portions when in the first position and a second orientation when in the second position. At least one of the first and second contact surface portions can also be movable relative to the support body. Accordingly, an operator can move the first and/or second contact surface portions to make minor adjustments to an angle at which material is removed from the workpiece, and can move the sample holder to make more substantial adjustments.

44 Claims, 3 Drawing Sheets

US 6,764,383 B1

METHODS AND APPARATUSES FOR PROCESSING MICROFEATURE WORKPIECE SAMPLES

TECHNICAL FIELD

The present invention relates generally to methods and apparatuses for processing microfeature workpiece samples.

BACKGROUND

During the development and production of microfeature workpieces, such as wafers, engineers periodically conduct destructive tests of selected workpieces to evaluate the efficacy of new and/or existing processes. One technique for carrying out such tests includes cutting a sample section from the microelectronic wafer, then grinding the sample to expose a feature of interest. The feature of interest is then examined with a transmission electron microscope (TEM). If necessary, the processes performed on subsequent wafers can be adjusted to correct any defects identified during the TEM examination.

FIG. 1 is partially schematic illustration of an apparatus 10 for performing the foregoing process. Such an apparatus is available from South Bay Technology of San Clemente, Calif. The apparatus 10 includes a body 11 into which two micrometer legs 20a, 20b are threadably inserted. The apparatus 10 can optionally include a third micrometer leg 20c. A sample holder 30 is fixedly attached to the body 11 and supports a sample 40, which is cut from a wafer. The apparatus 10 is then positioned adjacent to a grinding surface 51 of a grinding wheel 50. While the grinding wheel 50 rotates (as indicated by arrow R), an edge 39 of the sample 40 protruding from the sample holder 30 contacts the grinding surface 51, as do contact surfaces 21 of the micrometer legs 20a, 20b. Accordingly, the micrometer legs 20a, 20b can support the sample 40 in a fixed orientation relative to the grinding surface 51 while the sample 40 is ground down to expose the feature of interest.

FIG. 2 illustrates details of a sample 40 configured in accordance with the prior art. The sample 40 can have a plurality of active areas 43, each of which includes features of interest. Typical features of interest include container-shaped capacitors 44 that are electrically coupled to contacts 45 and are separated from an intermediate contact 47 by gate runners 46. It is typically desirable to grind the sample 40 down to a cleavage plane 48 to expose adjacent features within at least one of the active areas 43. Because the cleavage plane 48 is generally parallel to significant, readily visible features of the sample 40 (such as an array edge 41 or a metal runner 42), and because these features are typically aligned with a crystal plane of the wafer from which the sample 40 is extracted (as indicated by parallel axis X), it is relatively straightforward to precisely grind the sample 40 down to the cleavage plane 48 and expose the features of interest for TEM examination. For example, the sample 40 can be cut from its wafer by eye (i.e., without using a precise, machine-guided alignment process) so that the edge 39 of the sample 40 is at least approximately parallel to the cleavage plane 48. The operator can then iteratively: (a) adjust one of the micrometer legs 20a or 20b (FIG. 1) relative to the other; (b) grind the sample 40; and then (c) examine the edge of the sample 40 with reference to the array edge 41, the metal runner 42, or another easily visible feature parallel to the cleavage plane 48. Accordingly, the operator can orient the edge 39 of the sample 40 to be parallel with the cleavage plane 48. Once this orientation is obtained, the sample 40 can be ground down, as discussed above, until the features of interest at the cleavage plane 48 are exposed.

As the semiconductor industry moves to fit more active areas 43 into each wafer, some wafers have active areas 43 oriented such that the desired cleavage plane 48 exposed during destructive testing is no longer aligned with either the crystal plane (e.g., the X axis) or the easily visible features (e.g., the array edge 41 and/or the metal runner 42) of the sample 40. As a result, the initial cut that forms the edge 39 of the sample 40 is made at a significant angle relative to the X direction and the easily visible features. This operation can produce an initial cut that is misaligned by several degrees relative to the desired cleavage plane 48. Such a large misalignment is not easily corrected by the iterative method described above. For example, if the micrometer legs 20a, 20b, are adjusted to have significantly different lengths (to account for the initially misaligned cut), the corresponding contact surfaces 21 become highly faceted rather than flat (as indicated in an exaggerated fashion by phantom lines in FIG. 1). When the faceted micrometer legs 20a, 20b are subsequently rotated for further adjustment, the relative offset between the legs becomes unpredictable because the contact surfaces 21 are faceted rather than flat. This in turn can cause the sample 40 to be misoriented. If the sample 40 is not properly oriented, the desired features of interest will not be exposed during grinding, defeating the purpose for forming the sample.

DETAILED DESCRIPTION

A. Introduction

Figure 1:
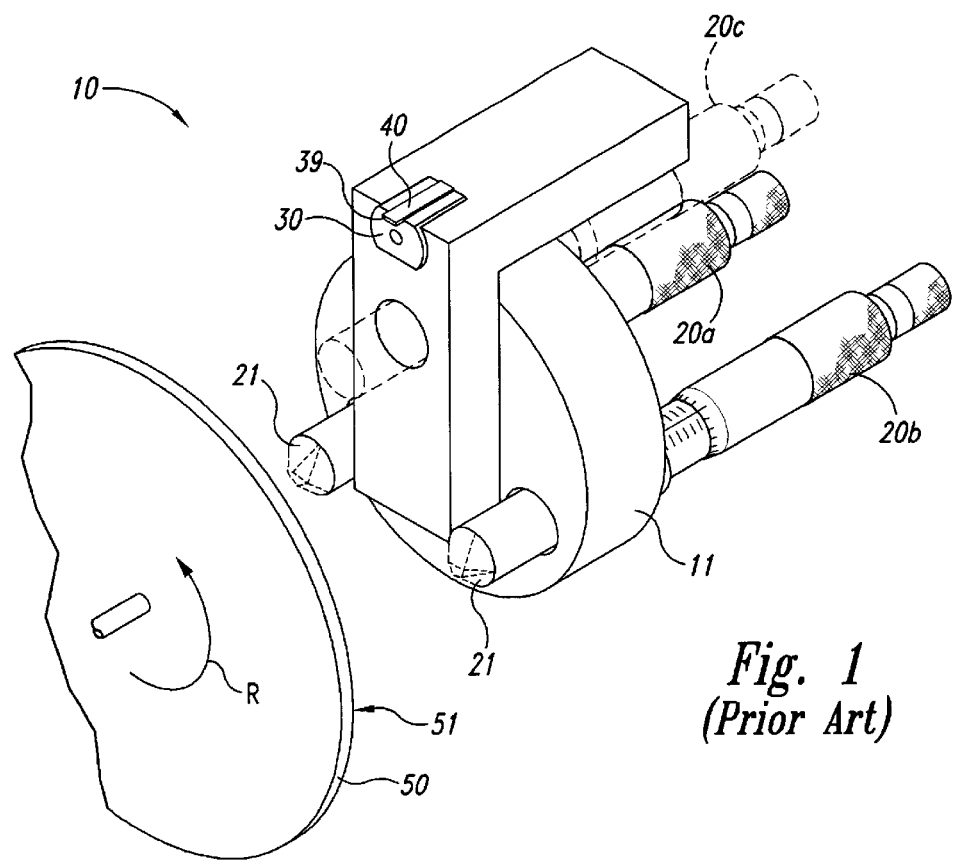
FIG. 1 is a partially schematic, isometric illustration of an apparatus for grinding microfeature workpiece samples in accordance with the prior art.

The present invention is directed to methods and apparatuses for processing samples of microfeature workpieces, for example, prior to microscopic inspection. The term "microfeature workpiece" is used throughout to include a workpiece formed from a substrate upon which and/or in which submicron circuits or components, and/or data storage elements or layers are fabricated. Submicron features in the substrate include but are not limited to trenches, vias, lines, contacts, and holes. These features typically have a submicron width (e.g., ranging from, for example, 0.1 micron to 0.75 micron) generally transverse to a major surface (e.g., a front side or a back side) of the workpiece. The term "microfeature workpiece" is also used to include a substrate upon which and/or in which micromechanical features are formed. Such features include read/write head features and other micromechanical elements having submicron or supramicron dimensions. In any of these embodiments, the workpiece substrate is formed from suitable materials, including ceramics, and may support layers and/or other formations of other materials, including but not limited to metals, dielectric materials and photoresists.

An apparatus in accordance with one aspect of the invention includes a support body, a first contact surface portion carried by the support body, and a second contact surface portion, also carried by the support body. The contact surface portions can be positioned to orient the support body relative to a reference surface, including an abrasive surface of a grinding wheel. At least one of the contact surface portions can be movable relative to the support body. A sample holder can be configured to releasably carry a microfeature workpiece sample and can be movable relative to the support body between a first position and a second position. The sample holder can have a first orientation relative to the first and second contact surface portions when in the first position, and a second orientation relative to the first and second contact surface portions when in the second position.

In other aspects of the invention, the apparatus can further include a securement device operatively coupled to at least one of the sample holder and the support body to releasably secure the sample holder at the first and second positions. The apparatus can still further include a shaft coupled to the support body, and the sample holder can be rotatably mounted to the shaft. The securement device can include a threaded rod operatively coupled to the sample holder to draw first and second portions of the sample holder around the shaft.

A method in accordance with another aspect of the invention includes releasably attaching a microfeature workpiece sample to a sample holder, with the sample holder being carried by a support body having a first contact surface portion and a second contact surface portion. The method can further include (a) moving at least one of the first and second contact surface portions relative to the other to change a first angle between the microfeature workpiece sample and a line passing through the first and second contact surface portions by first value, and (b) moving the sample holder relative to the support body to change a second angle between a target line of the sample and the line passing through the first and second contact surface portions by a second value. Material can then be removed from the sample at least toward the target line.

Methods in accordance with further aspects of the invention can include (a) threadably rotating at least one of a first leg (having the first contact surface portion) and a second leg (having the second contact surface portion) relative to the support body to change the first angle, and (b) rotating the sample holder relative to the support body to change the second angle. Methods in accordance with still further aspects of the invention can include examining the sample before moving the sample holder relative to the support body, and repeating the process of moving at least one of the first leg and the second leg relative to the support body until the line passing through the first and second contact surface portions is at least approximately parallel to a crystal orientation and/or a visible structure of the microfeature workpiece.

B. Apparatuses in Accordance with Embodiments of the Invention

Several specific details of the invention are set forth in the following description and in FIGS. 3–5 to provide a thorough understanding of certain embodiments of the invention. One skilled in the art, however, will understand that the present invention may have additional embodiments, and that other embodiments of the invention may be practiced without several of the specific features explained in the following description.

Figure 3:
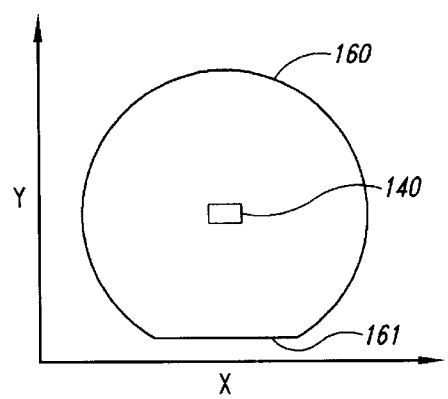
FIG. 3 is a top plan view of a microfeature workpiece from which a sample is extracted in accordance with an embodiment of the invention.

FIG. 3 is a partially schematic plan view of a microfeature workpiece 160 superimposed on orthogonal X and Y axes. The microfeature workpiece 160 includes a crystal orientation plane 161 that is at least approximately parallel to the X axis. After some or all of the processing steps required to produce features in the microfeature workpiece 160 are completed, a sample 140 can be extracted from the microfeature workpiece 160 and analyzed, for example, to determine the efficacy of the preceding manufacturing processes. FIGS. 4 and 5 illustrate further details of a representative sample 140, along with an apparatus for processing the sample 140 in accordance with an embodiment to the invention.

Figure 4:
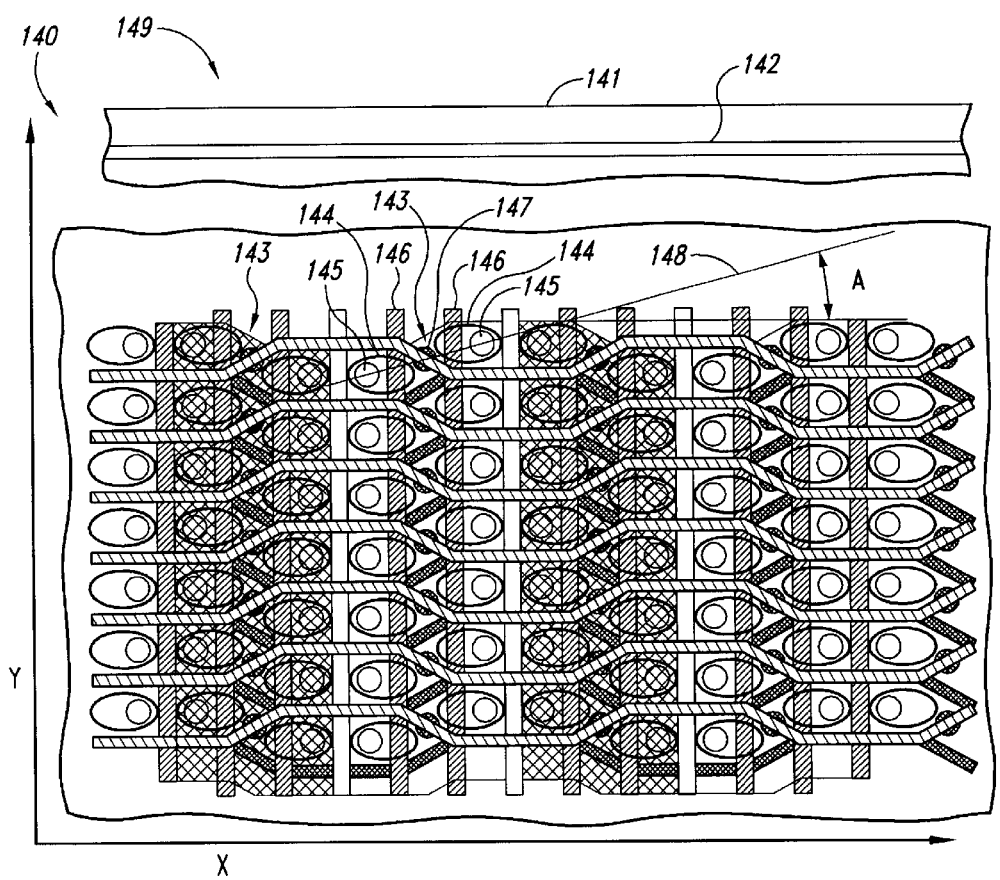
FIG. 4 is a partially schematic top plan view of a portion of the sample described above with reference to FIG. 3.

Referring next to FIG. 4, the sample 140 can include a plurality of arrays 149 (a portion of one is shown in FIG. 4), each having an array edge 141 aligned generally with the X axis. Metal runners 142, also aligned with the X axis, can provide electrical communication within and among adjacent arrays 149. Each array 149 can include a plurality of active areas 143. Each active area 143 can include microelectronic features, such as container-shaped capacitors 144 electrically coupled to contacts 145. An intermediate contact 147 can be positioned between adjacent capacitors 144 within an active area 143, and gate runners 146 can be provided between the contact 147 and the capacitors 144 to provide a plurality of transistors or other microelectronic devices.

After the foregoing features are fabricated (using, for example, existing deposition and chemical-mechanical planarization techniques), a method in accordance with an embodiment of the invention includes grinding away a portion of the sample 140 to expose selected features for microscopic examination. In one particular aspect of this embodiment, the selected features include the capacitors 145, the containers 144 and the contact 147 positioned within a given active area 143. Accordingly, the method can include grinding away a portion of the sample 140 to a target line 148 that passes through these features.

Figure 2:
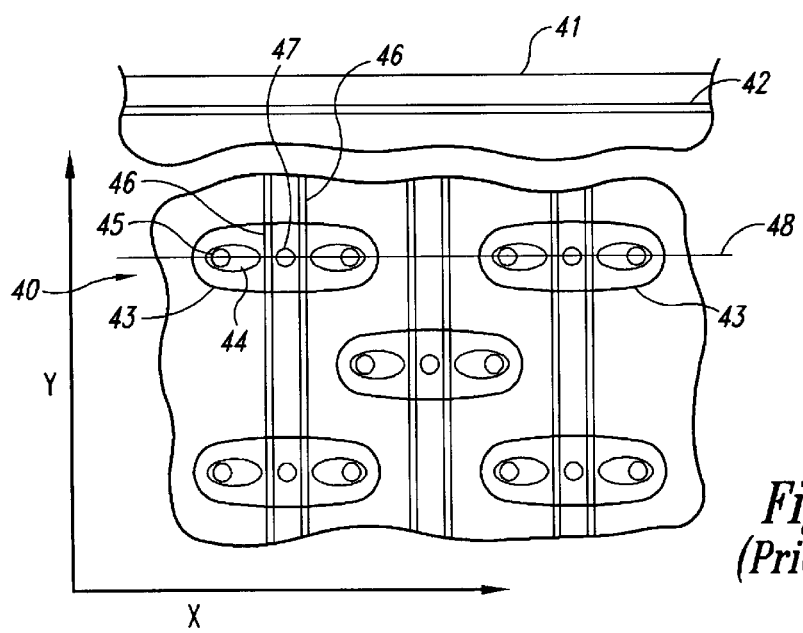
FIG. 2 is a partially schematic, top plan view of a portion of a microfeature workpiece sample configured in accordance with the prior art.

As shown in FIG. 4, the target line 148 can be oriented at a significant angle relative to the X axis. For example, in one embodiment, the target line 148 can be disposed at an angle A (relative to the X axis) having a value of approximately 18°. In other embodiments, angle A can have other values. For example, angle A can have a value of 26°, 17.5°, 17°, 10°, 90°, at least 5°, or other values, depending upon the manner in which the active areas 143 are positioned on the workpiece 160 (FIG. 3). In any of these embodiments, disposing the features of interest along a target line 148 that is inclined significantly relative to the X axis can result in a greater number of these features per unit area, which can advantageously reduce the size of the components formed in the microfeature workpiece 160. However, as described above with reference to FIGS. 1 and 2, it has been difficult to implement existing methods and apparatuses when grinding the sample 140 to a target line 148 that is significantly inclined relative to the X axis. As described below with reference to FIG. 5, an apparatus in accordance with an embodiment of the invention can overcome these difficulties.

Figure 5:
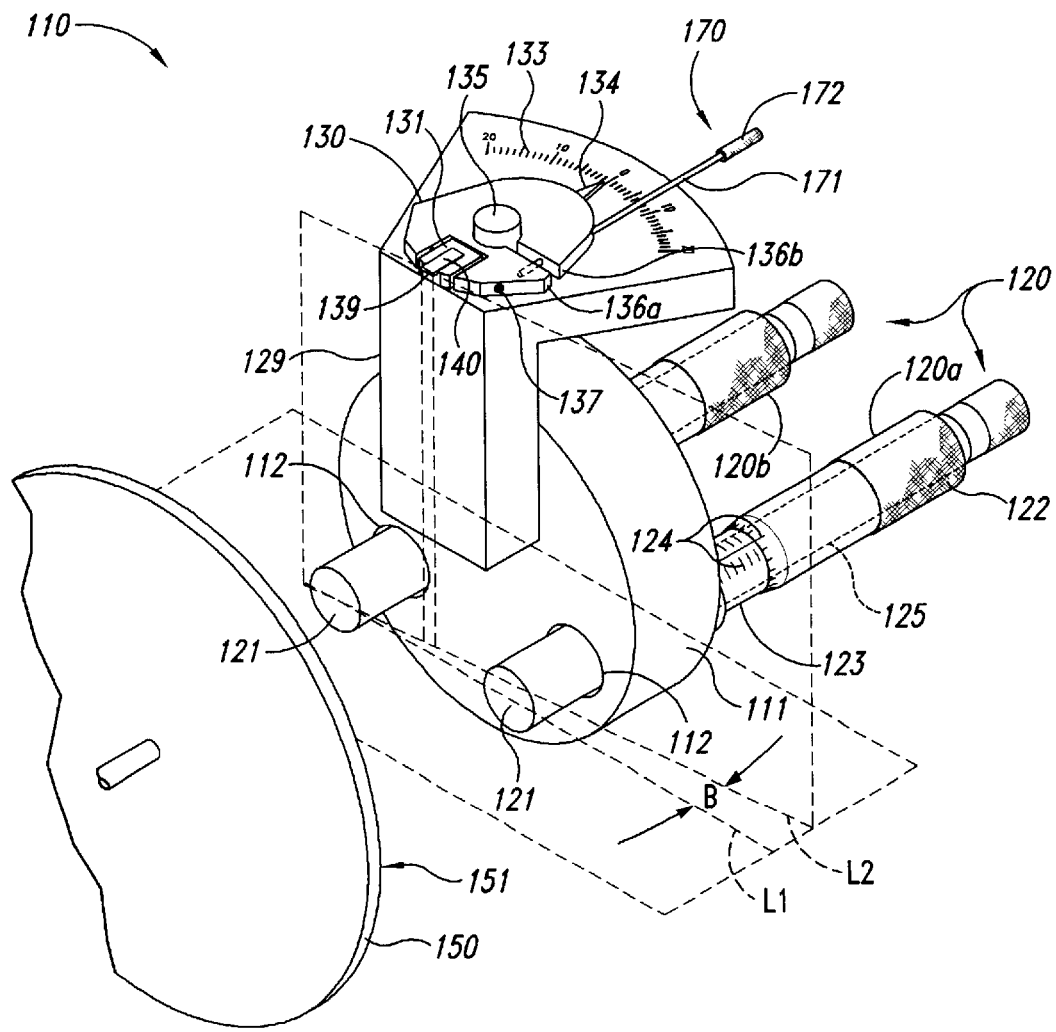
FIG. 5 is a partially schematic, isometric illustration of an apparatus for grinding a microfeature workpiece in accordance with an embodiment of the invention.

FIG. 5 is a partially schematic, isometric illustration of an apparatus 110 configured to support a sample 140 in accordance with an embodiment of the invention. In one aspect of this embodiment, the apparatus 110 includes a support body 111 having a bracket portion 129. The bracket portion 129 can carry a sample holder 130. The sample holder 130 can have a mounting portion 131 that carries the sample 140. In one aspect of this embodiment, the bracket portion 129 is fixed relative to the support body 111, and the sample holder 130 is movable relative to the bracket portion 129. As described below, an operator can accordingly move the sample holder 130 through relatively large angles to properly orient the sample 140 for grinding to the target line 148 described above.

In one aspect of an embodiment shown in FIG. 5, the sample holder 130 is rotatable relative to the support body 111. In a particular aspect of this embodiment, the bracket portion 129 can include a post 135 about which the sample holder 130 rotates. In a further aspect of this embodiment, the sample holder 130 can include a first portion 136a and a second portion 136b, each of which extends at least part-way around the post 135. The apparatus 110 can further include a securement device 170 that releasably secures the sample holder 130 in a particular angular orientation relative to the post 135. In one embodiment, the securement device 170 includes a rod 171 that passes through the second portion 136b and threadably engages the first portion 136a. The rod 171 can include a finger grip 172 which allows an operator to selectively clamp and unclamp the first and second portions 136a, 136b about the post 135 by rotating the rod 171. In other embodiments, the securement device 170 can have other arrangements.

In a further aspect of an embodiment shown in FIG. 5, at least one of the bracket portion 129 (or another structure fixed relative to the support body 111) and the sample holder 130 includes a scale or other visual indicator of the relative angular position between these components. For example, in a particular embodiment, the bracket portion 129 can include an angular scale 133 and the sample holder 130 can include a pointer 134 to indicate the angular position of the sample holder 130 relative to the bracket 129. In other embodiments, the relative locations of the angular scale 133 and the pointer 134 can be reversed, or the apparatus 110 can include other arrangements for visually indicating the angular position of the sample holder 130 relative to the support body 111 and/or the bracket 129.

The apparatus 110 can also include one or more adjustable legs 120 to provide for relatively minor angular adjustments, as described below. In a particular aspect of an embodiment shown in FIG. 5, the apparatus 110 can include two legs 120 (shown as a first leg 120a and a second leg 120b). In a further particular aspect of this embodiment, both legs 120 can be movable relative to the support body 111. In another embodiment, only one of the legs 120 is movable relative to the support body 111. In still a further embodiment, the apparatus 110 can include more than two legs 120. In one aspect of any of the foregoing embodiments, at least one of the legs 120 can be movable. Accordingly, the movable leg or legs 120 can include a shaft 125 that threadably engages a micrometer housing 123 on one side of the support body 111. The shaft 125 extends through the support body 111 and out through an aperture 112 on the opposite side of the support body 111. One end of the shaft 125 can be attached to a finger grip 122 to allow an operator to rotate the shaft 125 relative to the micrometer housing 123. The finger grip 122 and the micrometer housing 123 can include graduation markings 124 to indicate the axial travel of the shaft 125 as the finger grip 122 is rotated. The opposite end of the shaft 125 can include a contact surface portion 121 configured to undergo abrasive contact with a grinding wheel 150 as the sample 140 is processed.

In other embodiments, the apparatus 110 can have other arrangements for supporting the contact surface portions 121. For example, in one embodiment, the contact surface portions 121 can depend from a single movable structure, rather than two independently movable legs 120. In a particular aspect of this embodiment, the contact surface portions 121 can depend from a single structure that pivots about an axis generally parallel to the planes of the contact surface portions 121. When the structure is pivoted in one direction, one of the contact surface portions 121 moves forward relative to the other. When the structure is pivoted in the opposite direction, the one contact surface portion 121 moves aft relative to the other. In other embodiments, the apparatus 110 can have still further arrangements that allow the position of at least one contact surface portion 121 to be adjusted. In still further embodiments, the contact surface portions 121 can orient the support body 111 relative to a reference surface other than the grinding wheel 150.

In a particular aspect of an embodiment shown in FIG. 5, the sample 140 can be releasably attached to the mounting portion 131, for example, with an adhesive. The mounting portion 131 can be releasably attached to the sample holder 130 with a set screw 137. In another embodiment, the set screw 157 can be replaced with other releasable devices. In still further embodiments, the apparatus 110 can include other arrangements for supporting the sample 140. In any of these embodiments, an operator can rotate the sample 140 relative to the support body 111, as described in greater detail below.

C. Processes in Accordance with Embodiments of the Invention

A process in accordance with an embodiment of the invention is described below with reference to FIGS. 3–5. Beginning with FIG. 3, an operator can cut the sample 140 from the microfeature workpiece 160 such that the edges of the sample 140 are aligned at least approximately parallel with the X axis. Referring next to FIG. 5, the operator can then mount the sample 140 to the mounting portion 131. The legs 120 can be adjusted to be approximately flush with, or slightly offset from a projecting edge 139 of the sample 140. The operator can then position the apparatus 110 adjacent to an abrasive surface 151 of the grinding wheel 150, so that the contact surface portions 121 of the legs 120 and the edge 139 of the sample 140 contact the abrasive surface 151 as the grinding wheel 150 rotates.

During the next phase of the process, the operator can selectively remove material from the sample 140 to more precisely align the edge 139 with the X direction. For example, the operator can adjust at least one of the first and second legs 120a, 120b to adjust the angular orientation of the edge 139 relative to a line L1 passing through the contact surface portions 121. As shown in FIG. 5, the angular difference is represented by an angle B between line L1 and line L2, which is parallel to the edge 139. During grinding, the edge 139 becomes parallel to line L1 as the edge 139 and the contact surface portions 121 bear against the abrasive surface 151 of the grinding wheel 150. Referring now to FIGS. 4 and 5 together, the sample 140 can then be examined under a light scope or another suitable device to determine whether the edge 139 (FIG. 5) is parallel with the array edge 141, metal runner 142, or other easily visible feature known to be parallel to the X axis (see FIG. 4). The operator can adjust the first and/or second legs 120a, 120b and grind the sample 140 in an iterative manner until the edge 139 is at least approximately parallel to the X axis.

Once the edge 139 of the sample 140 is at least approximately parallel to the X axis, the operator can rotate the sample holder 130 relative to the support body 111 by the desired angle, and can activate the securement device 170 to lock the sample holder 130 at the desired location. The operator can again bring the apparatus 110 and the sample 140 into contact with the abrasive surface 151 to continue removing material from the sample 140, for example, until the target line 148 (FIG. 4) is reached and the features of interest are exposed. The features of interest can then be examined under a scanning electron microscope (SEM) or other suitable device. Optionally, the sample 140 can be removed from the apparatus 110 and thinned (by grinding the edge opposite the edge 139) while the sample 140 is supported on a separate sample holder. Accordingly, the thinned sample 140 can be examined under a transmission electron microscope (TEM) or other suitable device.

One feature of an embodiment of the apparatus 110 described above with reference to FIG. 5 is that both the sample holder 130 and at least one of the legs 120 are movable relative to the support body 111. Accordingly, at least one of the legs 120 can be moved by a relatively minor amount to precisely align the edge 139 of the sample 140 with the X direction. Once this orientation has been established, the sample holder 130 can be moved relative to the body 111 by a more substantial amount to align the target line 148 (FIG. 4) parallel to the abrasive surface 151 of the grinding wheel 150. As a result, the operator need not move one leg 120 relative to the other by a large distance. An advantage of this arrangement is that the contact surface portions 121 of the legs 120 are less likely to become highly faceted. Instead, the operator can move the legs 120 relative to each other by relatively small distances without causing major (and/or unexpected) changes between the relative locations of the corresponding contact surface portions 121, which can result when the contact surfaces 121 become highly faceted.

Another advantage of an embodiment of the foregoing arrangement is that the sample 140 can first be precisely oriented relative to easily visible features that are known to be parallel to the X axis, and can then be precisely rotated to the angle corresponding to a target line 148 that exposes the features of interest. As a result, the samples 140 can be consistently ground to the correct location, increasing the likelihood that a particular sample 140 will reveal the desired features of interest at the desired orientation.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. An apparatus for supporting a microfeature workpiece sample, comprising:
    a support body;
    a first contact surface portion carried by the support body;
    a second contact surface portion carried by the support body, wherein at least one of the first and second contact surface portions is movable relative to the support body, and wherein the first and second contact surface portions are positioned to orient the support body relative to a reference surface; and
    a sample holder configured to releasably carry a microfeature workpiece sample, the sample holder being movable relative to the support body between a first position and a second position, wherein the sample holder has a first orientation relative to the first and second contact surface portions when in the first position and a second orientation relative to the first and second contact surface portions when in the second position.

2. The apparatus of claim 1, further comprising:
    a first leg having the first contact surface portion; and
    a second leg having the second contact surface portion, wherein at least one of the first and second legs is movable relative to the support body.

3. The apparatus of claim 1, further comprising a securement device operatively coupled to at least one of the sample holder and the support body to releasably secure the sample holder at the first and second positions.

4. The apparatus of claim 1, further comprising:
    a shaft coupled to the support body, and wherein the sample holder is rotatably mounted to the shaft, further wherein the sample holder includes a first portion extending at least part-way around the shaft and a second portion extending at least part-way around the shaft; and
    a securement device operatively coupled to the sample holder, the securement device including a threaded rod threadably engaged with at least one of the first and second portions to draw the first and second portions toward each other around the shaft.

5. The apparatus of claim 1 wherein the sample holder is rotatable relative to the support body.

6. The apparatus of claim 1, further comprising:
    an angular scale having a fixed position relative to at least one of the sample holder and the support body; and
    a pointer having a fixed position relative to at least the other of the sample holder and the support body.

7. An apparatus for supporting a microfeature workpiece sample, comprising:
    a support body;
    a first leg having a first contact surface;
    a second leg having a second contact surface, wherein at least one of the first and second legs is movable relative to the support body to move at least one of the first and second contact surfaces relative to the support body; and
    a sample holder configured to releasably carry a microfeature workpiece sample, the sample holder being movable relative to the support body between a first position and a second position, wherein the sample holder has a first orientation relative to the first and second contact surfaces when in the first position and a second orientation relative to the first and second contact surfaces when in the second position.

8. The apparatus of claim 7, further comprising a securement device operatively coupled to at least one of the sample holder and the support body to releasably secure the sample holder at the first and second positions.

9. The apparatus of claim 7, further comprising:
    a shaft coupled to the support body, and wherein the sample holder is rotatably mounted to the shaft, further wherein the sample holder includes a first portion extending at least part-way around the shaft and a second portion extending at least part-way around the shaft; and
    a securement device operatively coupled to the sample holder, the securement device including a threaded rod threadably engaged with at least one of the first and second portions to draw the first and second portions toward each other around the shaft.

10. The apparatus of claim 7 wherein the first leg is movable relative to the support body to move the first contact surface relative to the support body, and wherein the second leg is movable relative to the support body to move the second contact surface relative to the support body.

11. The apparatus of claim 7 wherein the sample holder is rotatable relative to the support body.

12. The apparatus of claim 7, further comprising:
an angular scale having a fixed position relative to at least one of the sample holder and the support body; and
a pointer having a fixed position relative to at least the other of the sample holder and the support body.

13. The apparatus of claim 7 wherein the sample holder includes a mounting portion removably coupled to the sample holder, the mounting portion being configured to carry the sample.

14. The apparatus of claim 7, further comprising a grinding device having a grinding wheel positioned to engage the first and second contact surfaces.

15. The apparatus of claim 7 wherein the first and second contact surfaces are configured to undergo abrasive contact with a rotating grinding wheel.

16. An apparatus for supporting microfeature workpiece samples for grinding, comprising:
a support body;
a first leg having a first contact surface, the first leg being threadably engaged with the support body and rotatable relative to the support body to move the first contact surface relative to the support body;
a second leg having a second contact surface, the second leg being threadably engaged with the support body and rotatable relative to the support body to move the second contact surface relative to the support body;
a shaft coupled to the support body;
a sample holder rotatable about the shaft between a first position and a second position, the sample holder being configured to releasably carry a microfeature workpiece sample; and
a securement device operatively coupled to the sample holder and the support body to releasably secure the sample holder at the first and second positions.

17. The apparatus of claim 16, wherein the sample holder includes a first portion extending at least part-way around the shaft and a second portion extending at least part-way around the shaft, and wherein the securement device includes a threaded rod threadably engaged with at least one of the first and second portions to draw at least one of the first and second portions toward the other around the shaft.

18. The apparatus of claim 16, further comprising:
an angular scale having a fixed position relative to at least one of the sample holder and the support body; and
a pointer having a fixed position relative to at least the other of the sample holder and the support body.

19. The apparatus of claim 16 wherein the sample holder includes a mounting portion removably coupled to the sample holder, the mounting portion being configured to carry the sample.

20. The apparatus of claim 16, further comprising a grinding device having a grinding wheel positioned to engage the first and second contact surfaces.

21. The apparatus of claim 16 wherein the first and second contact surfaces are configured to undergo abrasive contact with a rotating grinding wheel.

22. A method for processing microfeature workpiece samples, comprising:

releasably attaching a microfeature workpiece sample to a sample holder, the sample holder being carried by a support body, the support body carrying a first contact surface portion and a second contact surface portion;
moving at least one of the first and second contact surface portions relative to the support body to change a first angle between the microfeature workpiece sample and a line passing through the first and second contact surfaces portions by a first value;
moving the sample holder relative to the support body to change a second angle between a target line of the sample and the line passing through the first and second contact surface portions by a second value; and
removing material from the sample at least toward the target line.

23. The method of claim 22 wherein changing the first angle by a first value includes changing the first angle by a first value less than the second value.

24. The method of claim 22 wherein removing material from the sample includes removing material at least to the target line.

25. The method of claim 22, further comprising removing material from the first and second contact surface portions while removing material from the sample.

26. The method of claim 22 wherein moving the sample holder includes rotating the sample holder relative to the support body.

27. The method of claim 22 wherein removing material from the sample includes grinding material from the sample.

28. The method of claim 22, further comprising releasably securing the sample holder relative to the support body after moving the sample holder relative to the support body.

29. The method of claim 22, further comprising:
before moving the sample holder relative to the support body, examining the sample; and
before moving the sample holder relative to the support body, repeating the process of moving at least one of the first and second contact surface portions relative to the support body until the line passing through the first and second contact surface portions is at least approximately parallel to a crystal orientation of the microfeature workpiece.

30. A method for processing microfeature workpiece samples, comprising:
releasably attaching a microfeature workpiece sample to a sample holder, the sample holder being carried by a support body, the support body having a first leg with a first contact surface, and a second leg with a second contact surface;
threadably rotating at least one of the first leg and the second leg relative to the support body to change a first angle between the microfeature workpiece sample and a line passing through the first and second contact surfaces by a first value;
rotating the sample holder relative to the support body to change a second angle between a target line of the sample and the line passing through the first and second contact surfaces by a second value; and
removing material from the sample at least to the target line.

31. The method of claim 30 wherein changing the first angle by a first value includes changing the first angle by a first value less than the second value.

32. The method of claim 30 wherein rotating the sample holder relative to the support body includes rotating the sample holder about a shaft, and wherein the method further comprises releasably securing the sample holder relative to the support body by clamping the sample holder to the shaft after moving the sample holder relative to the support body.

33. The method of claim 30, further comprising removing material from the first and second contact surfaces while removing material from the sample.

34. The method of claim 30 wherein removing material from the sample includes grinding material from the sample.

35. The method of claim 30, further comprising:
  before moving the sample holder relative to the support body, examining the sample; and
  before moving the sample holder relative to the support body, repeating the process of rotating at least one of the first leg and the second leg relative to the support body and removing material from the microfeature workpiece until the line passing through the first and second contact surfaces is at least approximately parallel to a crystal orientation of the microfeature workpiece.

36. The method of claim 30 wherein rotating the sample holder includes rotating the sample holder through an angle of at least seventeen degrees.

37. The method of claim 30 wherein rotating the sample holder includes rotating the sample holder through an angle of at least ten degrees.

38. The method of claim 30 wherein rotating the sample holder includes rotating the sample holder through an angle of at least five degrees.

39. A method for processing microfeature workpiece samples, comprising:
  separating a sample from a microfeature workpiece, the microfeature workpiece having a crystal orientation;
  releasably attaching the sample to a sample holder, the sample holder being carried by a support body, the support body having a first leg with a first contact surface and a second leg with a second contact surface;
  moving at least one of the first leg and the second leg relative to the support body and removing material from the sample until a line passing through the first and second contact surfaces is at least approximately parallel to the crystal orientation;
  moving the sample holder relative to the support body until the line passing through the first and second contact surfaces is oriented at a target angle relative to a target line of the sample; and
  removing material from the sample at least to the target line.

40. The method of claim 39, further comprising removing material from the first and second contact surfaces while removing material from the sample.

41. The method of claim 39 wherein moving the sample holder includes rotating the sample holder relative to the support body.

42. The method of claim 39 wherein removing material from the sample includes grinding material from the sample.

43. The method of claim 39, further comprising releasably securing the sample holder relative to the support body after moving the sample holder relative to the support body.

44. The method of claim 39, further comprising:
  before moving the sample holder relative to the support body, examining the sample; and
  before moving the sample holder relative to the support body, repeating the process of moving at least one of the first leg and the second leg relative to the support body and removing material from the microfeature workpiece until the line passing through the first and second contact surfaces is at least approximately parallel to a crystal orientation of the microfeature workpiece.

* * * * *